(12) United States Patent
Tsuzaki et al.

(10) Patent No.: US 7,378,114 B2
(45) Date of Patent: May 27, 2008

(54) METHOD FOR PRODUCING SOLUBLE COMPOSITION CONTAINING ISOFLAVONES

(75) Inventors: Shinichi Tsuzaki, Izumisano (JP); Hideo Araki, Izumisano (JP); Yukio Hashimoto, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 0 days.

(21) Appl. No.: 11/282,756

(22) Filed: Nov. 17, 2005

(65) Prior Publication Data

US 2006/0068042 A1    Mar. 30, 2006

Related U.S. Application Data

(60) Division of application No. 10/727,292, filed on Dec. 2, 2003, now abandoned, which is a continuation of application No. PCT/JP02/06252, filed on Jun. 21, 2002.

(30) Foreign Application Priority Data

Jun. 21, 2001    (JP) .............................. 2001-187783

(51) Int. Cl.
    *A61K 36/48*    (2006.01)

(52) U.S. Cl. ..................................................... 424/757
(58) Field of Classification Search ..................... None
    See application file for complete search history.

(56) References Cited

U.S. PATENT DOCUMENTS

| 5,994,508 | A | 11/1999 | Bryan et al. ................. 530/378 |
| 6,444,239 | B2 | 9/2002 | Obata et al. ................. 424/757 |
| 6,664,382 | B2 | 12/2003 | Waggle et al. ................. 536/8 |

FOREIGN PATENT DOCUMENTS

JP    10298175 A    11/1998

*Primary Examiner*—Christopher R. Tate
*Assistant Examiner*—Melenie McCormick
(74) *Attorney, Agent, or Firm*—J.C. Patents

(57) ABSTRACT

A method for producing a composition containing soluble isoflavones is described, which uses soybean materials as raw materials. The composition is obtained in a natural state without addition of solubilizing agents and chemical modification, and has high solubility under neutral to acidic conditions and good long-term stability under refrigeration. By removing the insoluble materials from the water-extract liquid of a soybean material having a pH value of 2-7 and a temperature of 0-17° C., a composition containing isoflavones can be efficiently obtained with high solubility under neutral to acidic conditions and good stability under refrigeration.

3 Claims, No Drawings

METHOD FOR PRODUCING SOLUBLE COMPOSITION CONTAINING ISOFLAVONES

CROSS-REFERENCE TO RELATED APPLICATION

This application is a divisional application of, and claims the priority benefit of, U.S. application Ser. No 10/727,292 filed on Dec. 02, 2003 now abandoned, which is a Continuation Application of an International Patent Application PCT/JP02/06252, filed on Jun. 21, 2002. The international application also claims the priority benefit of Japanese Basic Application No. 2001-187783 filed on Jun. 21, 2001.

BACKGROUND OF THE INVENTION

1. Field of the Invention

The present invention relates to a method for producing a composition containing soluble isoflavones.

2. Description of the Related Art

Soybean isoflavones are a group of compounds having a 3-phenylchromone skeleton that exist in soybeans. Specifically, soybean isoflavones are present in the forms of glucosides, malonyl glucosides, acetyl glucosides or aglycones, etc. The glucosides include daidzin, genistin and glycitin. The malonyl glucosides include 6"-O-malonyldaidzin, 6"-O-malonylgenistin and 6"-O-malonylglycitin. The acetyl glucosides include 6"-O-acetyldaidzin, 6"-O-acetylgenistin and 6"-O-acetylglycitin. The aglycones include daidzein, genistein and glycitein. The general structures and the species of the above compounds can be expressed by formulae (1)-(2) below:

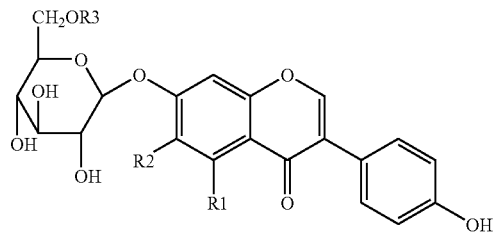
(1)

The group of compounds having the general skeleton expressed by formula (1)

| | R1 | R2 | R3 |
|---|---|---|---|
| daidzin | H | H | H |
| genistin | OH | H | H |
| glycitin | H | OCH$_3$ | H |
| 6"-O-malonyldaidzin | H | H | COCH$_2$COOH |
| 6"-O-malonylgenistin | OH | H | COCH$_2$COOH |
| 6"-O-malonylglycitin | H | OCH$_3$ | COCH$_2$COOH |
| 6"-O-acetyldaidzin | H | H | COCH$_3$ |
| 6"-O-acetylgenistin | OH | H | COCH$_3$ |
| 6"-O-acetylglycitin | H | OCH$_3$ | COCH$_3$ |

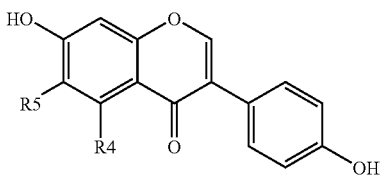
(2)

The group of compounds having the general skeleton expressed by formula (2)

| | R4 | R5 |
|---|---|---|
| daidzein | H | H |
| genistein | OH | H |
| glycitein | H | OCH$_3$ |

The above isoflavones are known to have estrogen-like functions and antioxidative functions, etc., and therefore get worldwide attentions as food components effective to prevent cancer and osteoporosis or alleviate the menopausal syndrome. However, isoflavone is difficult to dissolve in water, and its solubility in water is 0.002-0.003 g under 25° C. according to the literature. Consequently, cloudiness or precipitation easily occurs in or after the manufacturing process of food products, especially drink products or dessert products, etc, and the applications of isoflavones are restricted in these fields. Therefore, improvement in the solubility of isoflavones is required.

To solve the above problem, for example, Japanese Patent Application Laid Open No. 09-309902 or 10-298175 discloses a method that includes isoflavone molecules in cyclodextrin to improve its solubility in water. However, since it is necessary to previously refine the isoflavones to certain purity in the method, the operation steps are complicated. Moreover, since cyclodextrin is used when isoflavones are added into drink products, the aroma components like flavors are also included in cyclodextrin together with the isoflavone molecules. Therefore, the balance of aroma is easily broken down, and the commercial product design is difficult accordingly. Moreover, isoflavones cannot be dissolved in water in a high concentration due to the limitation of the solubility of cyclodextrin. On the other hand, Japanese Patent Application Laid Open No. 2000-325043 discloses another method that dissolves isoflavones by heating the compounds together with a solubilizing agent consisting of dehydrated or hydrated propylene glycol and/or octenylsuccinic acid starch in the presence of water. Nevertheless, the food additives like propylene glycol and octenylsuccinic acid starch are not preferable to use in latest years. Moreover, Japanese Patent Application Laid Open No. 2000-327692 discloses a method for improving the solubility of isoflavones in water, which forms α-glycosylisoflavone derivatives utilizing a glycosyltransferase in the presence of an α-glycosylsaccharide compound like dextrin. The α-glycosylisoflavone derivative is formed by attaching a glucose residue to a daidzin or genistin molecule with an α-1,4 bond. However, since one or more equivalents of the α-glycosylsaccharide compound must be used to bond with the isoflavone molecules, the process is complicated. Moreover, the percentage of isoflavones in total solid content is surely lowered in the method, and there is no isoflavone molecule present in its natural state. Furthermore, though the solubility and the long-term stability under low temperature both are important properties when a composition containing isoflavones is added in a liquid food product like a drink product, there is no information about them. Each of the aforementioned methods solubilizes isoflavones either by adding a solubilizing agent or by chemically modifying isoflavone molecules to form soluble derivatives, while there is no easier method suitably used for industrial production that solubilizes insoluble isoflavones in their natural form within a wide pH range.

SUMMARY OF THE INVENTION

In view of the foregoing, one object of this invention is to provide a method for producing a composition containing soluble isoflavones, wherein soybean materials are used as raw materials and isoflavones are extracted in their natural forms without addition of solubilizing agents and chemical modification. The composition containing soluble isoflavones has high solubility over a wide pH range, and has good long-term stability under refrigeratory preservation.

In the study of the aforementioned issue, the inventors discovered that the isoflavones in soybeans can be easily extracted with water even though their solubilities are low. Meanwhile, it is absolutely surprising that the isoflavones can be solubilized steadily even in a high-concentration state. After repeating the outstanding study, it is confirmed that by adjusting the pH value of the soybean extract liquid obtained from soybean materials to 5.5-7 and cooling the soybean extract liquid to 0-17° C. and then removing the insoluble materials thus produced, a composition containing isoflavones that has a good solubility under neutral to weak acidic conditions and good long-term stability under refrigeratory preservation can be obtained with a higher recovery ratio. Moreover, when the pH value of the soybean extract liquid is adjusted smaller than 5.5, a composition containing isoflavones that has a good solubility under acidic conditions can also be obtained by removing the insoluble materials. However, since a lot of the isoflavones precipitate together with proteins under the condition, the recovery ratio of isoflavones is low. By treating the soybean extract liquid with proteases and removing the insoluble materials produced under an acidic low-temperature condition, precipitation of isoflavone can be prevented, and a composition containing isoflavones that has a good solubility under acidic conditions and good long-term stability under refrigeratory preservation can be obtained with a higher recovery ratio. The present invention is completed based on the above discovery.

That is, this invention is directed to 1) a method for producing a composition containing soluble isoflavones from a soybean extract liquid, featuring with removal of insoluble materials from the soybean extract liquid that has a pH value adjusted to 2-7 and a temperature adjusted to 0-17° C.; 2) a method for producing a composition containing soluble isoflavones according to 1), wherein the amount of isoflavones in total solid content of the soybean extract liquid is 0.2-20 wt %, the crude protein content is 30 wt % or less, and the amount of lipids is 4 wt % or less; 3) a method for producing a composition containing soluble isoflavones according to 1) or 2), wherein the process of preparing the soybean extract liquid includes adjusting the pH value to 5.5-7 without a protease treatment; and 4) a method for producing a composition containing soluble isoflavones according to 1) or 2), wherein the process of preparing the soybean extract liquid includes a step of adjusting the pH value to satisfy the equation "$2 \leq pH \leq 5.5$" and a protease treatment.

It is to be understood that both the foregoing general description and the following detailed description are exemplary, and are intended to provide further explanation of the invention as claimed.

DESCRIPTION OF THE PREFERRED EMBODIMENTS

The present invention is specifically described as follows. The composition containing soluble isoflavones of this invention is prepared from a soybean extract liquid, which is obtained by treating soybean materials with an extracting solvent.

The soybean materials serving as the raw materials in this invention include whole soybeans, dehulled soybeans, dehulled and dehypocotyled soybeans, soybean hypocotyls, defatted soybeans and defatted soybean hypocotyls, etc. Particularly, the soybean hypocotyls contain more isoflavones than the other soybean materials, approximately in an amount of 1-2 wt %, an is therefore a suitable raw material for producing a composition containing a high concentration of isoflavones. Generally, soybean materials can be subjected to desired pre-treatments including physical treatments like pulverization, flattening and puffing treatments, dry-heating treatments like roasting treatment, wet-heating treatments like steaming treatment, heating treatments like drying treatment, and chemical treatments, etc. However, the physical treatments like pulverization, flattening and puffing treatments are preferably controlled not to destroy the soybean cells, or are preferably not performed at all. When physically treated raw material is subjected to water extraction, additional components other than isoflavones contained in the raw material, such as proteins or oils, easily exude in large amounts. Therefore, the solubility of the composition containing isoflavones is lowered, or the recovery ratio of isoflavones is lowered in the step of removing the insoluble materials. However, by using the method provided in this embodiment, exudation of proteins or lipids from the raw material can be inhibited.

Moreover, when soybean hypocotyls are used as the raw material, the unique grassy smell and astringent smell of unheated soybean hypocotyls will remain if the extraction operation is directly done to raw soybean hypocotyls. To reduce such smells, a heating treatment is preferably conducted, while the heating treatment should be controlled so that the soybean hypocotyls are not scorched to cause a bitter taste. The heating method can be any well-known method like a dry-heating method or a wet-heating method. For example, a dry-heating step of soybean hypocotyls can be conducted using a gas roaster (manufactured by Fuji Royal Corporation), an electroheating roaster (by Nippon Glass Corporation), a hot-blast roaster (by Buhler Corporation), a microwave heater (by New Japan Radio Co., Ltd.), or an indirect heating-type cooker, etc. The temperature of the heating treatment is preferably 100° C. or higher. The degree of heating can be specified as the water content of the soybean hypocotyls, and the heating treatment can be terminated when the water content is reduced to 1-9.5 wt %, preferably 3-9 wt %. On the other hand, a wet-heating process of soybean hypocotyls may utilize any method that conducts heating under a moderate amount of water without dissolving the isoflavones. Except steaming treatments, the methods that conduct heating after a hydration treatment or similar methods can also be used. When a steaming treatment is adopted, for example, the steaming apparatuses generally used in food industry, such as autoclaves, cookers or steam peelers, etc., can also be used.

Moreover, before isoflavones are extracted from the aforementioned soybean materials by water, the soybean materials are preferably subjected to a pre-treatment that uses an aqueous solvent of 4-80° C., preferably 4-40° C., to contact and wash the soybean materials. The aqueous solvent can be water, a solution of a salt or a buffer solution, etc., wherein the salt may be a calcium salt, a sodium salt or a potassium salt, etc., and the buffer solution may be a phosphoric acid buffer solution, a carbonic acid buffer solution or a citric acid buffer solution, etc. The pre-treatment is for removing the soluble components other than isoflavones in advance, including soluble nitrogen-free substances, nitrogen compounds and ash, etc., so as to increase the concentration of isoflavones in the soybean extract liquid. In the pre-treatment, it is not preferred to set the temperature under 4° C. even though such temperatures can still make sufficient cleaning effect, since the cost for the cooling operation will be increased to lower the utility. In the washing process, the weight ratio of the soybean material to water is not particularly restricted, and is generally 1:3-1:30, preferably 1:5-1:15. The contact time with water is moderately adjusted so that the extracted amount of the soluble components other than isoflavones in the liquid part is maximized, and is generally 5-240 minutes. The methods for contacting with water include various methods as the aforementioned water-extraction methods do, such as batch-type methods, continuation-type methods, counterflow-type methods and multistage-type methods. After the washing step is performed as above, the liquid part can be removed with a solid-liquid separation method like filtration or centrifugal separation, and the residue, i.e., the soybean material, is recovered.

Next, a method for obtaining a soybean extract liquid is described, wherein isoflavones are extracted from soybean materials or the pre-treated soybean materials mentioned above. The extracting solvent can be an aqueous solvent like water or an alcohol containing water. However, when the alcohol concentration in the solvent is high, the bad-taste components in soybeans including oils and phenol species, etc., are easily extracted simultaneously. Therefore, to obtain a good-taste extract with a required solubility, it is preferred to use water in the extraction step. The extraction method can be the one disclosed in Japanese Patent Application Laid Open No. 2000-14348. More specifically, the extraction process is preferably conducted at a temperature that is usually set for water-extraction of isoflavones. When the temperature is overly low, the recovery ratio of isoflavones is lowered, and the manufacturing process is inefficient. Therefore, the extraction temperature is usually 80° C. or higher, and is preferably 80-150° C. and more preferably 80-100° C. In the extraction process, the weight ratio of the raw material to water is not particularly restricted, and is usually 1:3-1:30, preferably 1:5-1:15. The contact time with water is moderately adjusted so that the extracted amount of isoflavones is maximized, and is generally 5-60 minutes. Moreover, sodium hydroxide, potassium hydroxide, sodium bicarbonate or sodium carbonate, etc., can be added as required to make an alkaline condition having a pH value of 8 or larger during the extraction process, so that the efficiency of isoflavone extraction can be improved. However, since some undesired components like proteins are also easily extracted under the condition, the pH value is suitably adjusted to 6-8, more preferably 6.5-7.5. Furthermore, a surfactant like glycerin fatty acid ester or sorbitane fatty acid ester, etc., can also be added in an amount of 0.01-1.0 w/v % relative to the water. The extraction methods include various methods, such as batch-type methods, continuation-type methods, counterflow-type methods and multistage-type methods, and the extraction efficiency can be improved with stirring. In addition, the extract liquid can be used as the extracting solvent of a new batch of soybean material.

After the extraction process is performed as above, a soybean extract liquid is obtained with a solid-liquid separation method like filtration or centrifugal separation, etc. Moreover, except the aforementioned soybean extract liquid, the soybean-immersed waste solution produced during manufacture of tofu or soybean milk or the soybean-boiled waste solution produced during manufacture of boiled soybeans, etc., can also be used as a soybean extract liquid. Moreover, it is preferably not to squeeze the extraction residue during the solid-liquid separation to prevent the proteins and the oils contained inside from exuding.

In the soybean extract liquid obtained as above, the amount of isoflavones in total solid content is usually 0.2-20 wt %, and the crude protein content in total solid content is 30 wt % or less, preferably 25 wt % or less. The lipid content in total solid content is 4 wt % or less, preferably 2 wt % or less. In the soybean milk obtained by pulverizing and extracting sovbeans, for example, the crude protein content in total solid content is usually 40-55 wt %, and the lipid content in total solid content is 25-35 wt %. Accordingly, it is confirmed that the exudation of crude proteins and lipids is inhibited during the extraction process for obtaining the soybean extract liquid of this invention.

Thereafter, the pH value of the soybean extract liquid obtained as above is adjusted to 2-7, and the soybean extract liquid is cooled to 0-17° C., preferably 0-10° C., and kept at the same temperature for 10 minutes or more, preferably 30 minutes or more, whereby some low-temperature insoluble materials are formed. If the pH value is adjusted smaller than 2, the isoflavones may self-decompose. On the other hand, the solubility of isoflavones gets low under a neutral to acidic condition having a pH value larger than 7. The pH value can be adjusted to any value within the range of 2-7, and may be adjusted to be equal to or smaller than that of the product into which the composition containing isoflavones will be added. When the cooling temperature is higher than 17° C., precipitation or cloudiness occurs even if the pH value of-the soybean extract liquid is adjusted to be equal to or smaller than that of the product. The acid for adjusting the pH value to 2-7 can be any one among the inorganic acids and the organic acids that are usually added in food. The applicable acids include hydrochloric acid, sulfuric acid, phosphoric acid, acetic acid, malic acid, tartaric acid, citric acid and ascorbic acid, etc., wherein hydrochloric acid is particularly preferable. Subsequently, the insoluble materials are removed with, for example, filtration or centrifugal separation, and a composition containing soluble isoflavones is obtained thereby. Generally, when proteins and other components get insoluble and precipitate because of cooling effect, the isoflavones contained in the soybean extract liquid easily co-precipitate with them. However, since the raw material used in this invention is not subjected to a physical treatment like pulverization, exudation of proteins and other components from the raw material can be inhibited to prevent co-precipitation. Therefore, the recovery ratio of isoflavones is not lowered.

On the other hand, there is no problem that the pH value of the soybean extract liquid is 5.5 or larger during removal of the insoluble materials. However, in the cases where the soybean extract liquid is made acidic with a pH value smaller than 5.5, the isoflavones easily co-precipitate with the proteins contained in the solution due to the interaction with the proteins when the proteins precipitate at the isoelectric point. This co-precipitation effect and the aforementioned co-precipitation phenomenon caused by low temperature synergistically lower the recovery ratio. As found by the inventors, when the pH value of the extract liquid of the soybean material is adjusted under 5.5, the amount of isoflavones in the soybean extract liquid is reduced by a half after the produced insoluble materials are removed.

To prevent co-precipitation of isoflavones and to improve the solubility of isoflavones under acidic condition in the aforementioned cases, the soybean extract liquid is preferably treated with proteases to decompose proteins into lower molecules. Meanwhile, the pH value of the soybean extract liquid is adjusted to satisfy the equation "$2 \leq pH \leq 5.5$", and the temperature of the same is set to 0-17° C. in the step of removing insoluble materials.

The species of the protease and the treating process using the same are not particularly restricted in the aforementioned cases, and endo-proteases or exo-proteases can be used. Generally, neutral proteases or alkaline proteases are preferably used to treat the soybean extract liquid, since the pH value of the soybean extract liquid is 6-7. Moreover, since β-glucosidase is present in proteases as an impurity, the β-glucoside bond between the aglycone moiety and the saccharide moiety of the isoflavone glucoside is broken in the aforementioned process, and the aglycones including daidzein, genistein and glycitein are released. Since the aglycones generally have lower solubilities as compared with glucosides, they are not desired. Therefore, the source of proteases is preferably an animal or plant source that has a low β-glucosidase activity, while a microorganism source is also feasible if only the β-glucosidase activity thereof is low. Moreover, the protease treatment is most preferably conducted after the soybean extract liquid is prepared and before the pH value of the same is adjusted to one of acidity. Though the protease treatment can be performed simultaneously with the pre-treatment wherein the soybean material is made contact with low-temperature water before the extraction stage, or simultaneously with the extraction stage using thermostable proteases, the proteins are decomposed into lower molecules and are extracted in a large amount. Moreover, it is also feasible to use acidic proteases after the soybean extract liquid is made acidic. However, since the proteins get insoluble because of precipitation at the isoelectric point, the effect of the proteases is extremely reduced.

The conditions of the protease treatment are not restricted if only they can meet the requirement of decomposing the proteins in the soybean extract liquid into lower molecules. The added amount of proteases is moderately adjusted with a titer, and is usually 0.01-10 wt % of the total solid content in the soybean extract liquid. The reaction conditions are moderately adjusted according to the optimum conditions of the used protease. Generally, the pH value is preferably adjusted to 6-8 when a neutral protease is used in the treatment, or is preferably adjusted to 8-10 when an alkaline protease is used. The treating temperature is preferably 40-60° C., and the treating time is preferably 0.5-5 hours. The reaction is terminated usually by performing a heating treatment above 80° C. to deactivate the enzyme.

The composition containing soluble isoflavones obtained as above can be directly used after the concentration thereof is properly adjusted. The composition may also be used in the form of condensed extract after being neutralized as required and condensed, or in the form of dry matter after a further drying process like a freeze-drying process or a spray-drying process, etc. Moreover, if required, a further process like a purification process using an adsorbent or a separation process using a solvent can be performed to produce a composition containing soluble isoflavones of higher purity. The adsorbent used in the purification process can be of polystyrene type, methacryl type or ODS type, etc, and the solvent used in the separation process can be butanol or the like.

When the amount of isoflavones in total solid content is 0.2-10 wt % in the composition and the composition is used in a product having a pH value larger than that on removing insoluble materials, cloudiness or precipitation does not occur even if the product is refrigerated under 10° C. That is, the composition shows high stability and a good solubility. The solubility of pure isoflavone in water is merely 0.002-0.003 g, while that of the isoflavones in the composition containing soluble isoflavones of this invention is 0.3 g or more (0.3-10 g). That is, it is possible to dissolve a large amount of isoflavones that is 100 or more times the amount in the prior art. Therefore, all neutral to weak acidic food products, such as neutral drinks like tea drinks or weak acidic drinks like coffee as well as ice cream and dessert, etc., can be applied with high concentrations of isoflavones without loss of transparency. In addition, the solubility in this invention is defined as the maximal amount of a solute dissolved in a solvent of 100 g under 25° C.

By using the method of this invention, the solubility issue of isoflavones in the prior art can be completed solved. Therefore, the scope of the applications of isoflavones can be significantly expanded.

Moreover, in this invention, the quantification of isoflavones is based on the standard analysis method of soybean isoflavone food product specifications issued by Japan Health Food & Nutrition Food Association, which is used to measure the total amount of 12 kinds of isoflavone compounds as follows. The amount of crude proteins is measured with the Kjeldahl method, and the amount of lipids with an extraction method using a chloroform-methanol mixed solvent.

<Method for Quantifying Isoflavones>

A sample containing approximately 1-10 mg of isoflavones is pulverized as required and precisely weighed, and is added with 25 ml of 70% (v/v) ethanol. The extraction process is conducted with stirring under room temperature for 30 minutes, and then an extract liquid is obtained with centrifugal separation. The residue is further subjected to the same extraction operation twice, and then the extract liquid of the three times is added with 70% (v/v) ethanol to prepare a sample solution of 100 ml. The sample solution is filtered with a filter of 0.45 μm and then analyzed with high-performance liquid chromatography (HPLC) under the following conditions:

Column: YMC-Pack ODS-AM303 (4.6×250 mm)
Mobile Phase: Acetonitrile:water:acetic acid=15:85:0.1–35:65:0.1 (v/v/v)
Flow rate: 1.0 ml/min
Temperature: 35° C.
Detection: UV (254 nm)
Injected amount: 10 μL A daizin standard is used to measure the daizin-converted concentrations of 12 kinds of isoflavones, and each measured value is multiplied with a corresponding quantification coefficient listed below to calculate the correct concentration of the corresponding isoflavone compound. The isoflavone quantification coefficient is 1.000 for daizin, 0.814 for genistin, 1.090 for glycitin, 1.444 for malonyldaizin, 1.095 for malonylgenistin, 1.351 for malonylglycitin, 1.094 for acetyldaizin, 1.064 for acetylgenistin, 1.197 for acetylglycitin, 0.583 for daizein, 0.528 for genistein, and 0.740 for glycitein. The total amount of isoflavones is then obtained by summing up the concentrations of all isoflavone compounds.

EXAMPLES

Some examples of this invention are described as follows. The examples are intended to exemplify the technical principles of this invention, but not to restrict the scope of this invention.

Experiment 1

100 g of whole soybeans from the America is added with 500 ml of water in a pre-treatment, wherein the soybeans contact with water under 20° C. for 2 hours. The liquid part is then removed with filtration. Next, the residue is added with 500 ml of water to implement an extraction process under 98° C. for 20 minutes, and then an extract liquid is obtained with filtration. The residue is further added with 500 ml of water to implement another extraction process under 98° C. for 20 minutes, and then another extract liquid is obtained with the same operation. The two extract liquids are mixed into a soybean extract liquid. In the soybean extract liquid, the amount of isoflavone in total solid content is 1.3 wt %, the crude protein content is 24 wt %, and the lipid content is 1.0 wt %. Subsequently, the soybean extract liquid is cooled to 20-0° C., as shown in Table 1, and then placed still for 30 minutes, while the pH value is 6.5 at the moment. Thereafter, the insoluble materials are removed with centrifugal separation, and the soybean extract liquid is freeze-dried into powder. The solubility of isoflavones in 100 g of water under 25° C. is then measured using the composition containing isoflavones. Moreover, a stability test is done by dissolving an equivalent amount of powder containing 10 mg of isoflavones in 100 ml of water, adjusting the pH value of the solution to 7-5.5 with sodium bicarbonate or citric acid, performing heat sterilization under 95° C. for 15 minutes and then preserving the solution under 10° C. for a month. The results are shown in Table 1.

TABLE 1

| Separation temperature (° C.) | Solubility of isoflavones (g) | Stability test | | |
|---|---|---|---|---|
| | | pH = 7 | pH = 6 | pH = 5.5 |
| 20 | >0.3 | X | X | X |
| 15 | >0.3 | ○ | ○ | ○ |
| 10 | >0.3 | ○ | ○ | ○ |
| 0 | >0.3 | ○ | ○ | ○ |

Evaluation for stability test: ○: without precipitation; X: precipitation occurs As shown in Table 1, when the insoluble materials are removed from the soybean extract liquid at a temperature under 20° C., the solubility of the composition containing isoflavones in water is significantly increased. Moreover, the results of the stability test indicate that excellent stability is achieved under neutral (pH=7) to weak acidic (pH=5.5) conditions.

Experiment 2

10 g of whole soybeans from the America is added with 500 ml of water in a pre-treatment, wherein the soybeans contact with water under 20° C. for 2 hours. The liquid part is then removed with filtration. Next, the residue is added with 500 ml of water to implement an extraction process under 98° C. for 20 minutes, and then an extract liquid is obtained with filtration. The residue is further added with 500 ml of water to implement another extraction process under 98° C. for 20 minutes, and then another extract liquid is obtained with the same operation. The two extract liquids are mixed into a soybean extract liquid, which has a pH value of 6.5 at the moment. In the soybean extract liquid, the amount of isoflavone in total solid content is 1.3 wt %, the crude protein content is 24 wt %, and the lipid content is 1.0 wt %. Next, a neutral protease from *Bacillus subtilis* (Orientase 90N, produced by Hankyu Kyoei Bussan Inc.) is added in an amount of 0.9 wt % relative to the total solid content, and the reaction is carried out under 50° C. for 1 hour. Next, the soybean extract liquid is heated under 80° C. for 30 minutes to deactivate the enzyme, and the pH value and temperature of the soybean are adjusted as in Table 2, wherein the pH value is adjusted by adding $HCl_{(aq)}$. The soybean extract liquid is then placed still for 30 minutes to complete the acid-precipitation reaction. Thereafter, the insoluble materials are removed with centrifugal separation, and the soybean extract liquid NaOH is neutralized by adding NaOH to have a pH value of 6.5. The soybean extract liquid is then freeze-dried into powder. The solubility of isoflavones in 100 g of water under 25° C. is then measured using the composition containing isoflavones. Moreover, a stability test is done by dissolving an equivalent amount of powder containing 10 mg of isoflavones in 100 ml of water, adjusting the pH value of the solution to 7-3.5 with sodium bicarbonate or citric acid, performing heat sterilization under 95° C. for 15 minutes and then preserving the solution under 10° C. for a month. The results are shown in Table 2.

TABLE 2

| pH value for separation | Cooling temperature (° C.) | Solubility of isoflavones (g) | pH value in stability test | | | | |
|---|---|---|---|---|---|---|---|
| | | | 7 | 6 | 5.5 | 4.5 | 3.5 |
| 5.5 | 20 | >0.3 | X | X | X | X | X |
| 5.5 | 15 | >0.3 | ○ | ○ | ○ | X | X |
| 4.5 | 20 | >0.3 | ○ | ○ | ○ | X | X |
| 4.5 | 15 | >0.3 | ○ | ○ | ○ | ○ | X |
| 3.5 | 20 | >0.3 | ○ | ○ | ○ | X | X |
| 3.5 | 15 | >0.3 | ○ | ○ | ○ | ○ | ○ |
| 2.0 | 15 | >0.3 | ○ | ○ | ○ | ○ | ○ |

Evaluation for stability test: ○: without precipitation; X: precipitation occurs As shown in Table 2, when the insoluble materials are removed from the soybean extract liquid at a pH value smaller than 5.5 and a temperature under 20° C., the solubility of the composition containing isoflavones in water is significantly increased as compared with pure isoflavones. Moreover, the results of the stability test indicate that excellent stability is achieved under neutral (pH=7) to acidic (pH=3.5) conditions.

Example 1

100 g of whole soybeans from the America, in which the amount of isoflavones is 0.2 wt %, is added with 500 ml of water in a pretreatment, wherein the soybeans contact with water under 20° C. for 2 hours. The liquid part is then removed with filtration. Next, the residue is added with 500 ml of water to implement an extraction process under 98° C. for 20 minutes, and then an extract liquid is obtained with filtration. The residue is further added with 500 ml of water to implement another extraction process under 98° C. for 20 minutes, and then another extract liquid is obtained with the same operation. The two extract liquids are mixed into a soybean extract liquid. In the soybean extract liquid, the amount of isoflavone in total solid content is 1.3 wt %, the crude protein content is 24 wt %, and the lipid content is 1.0 wt %. The soybean extract liquid is cooled to 10° C. and kept at the same temperature for 30 minutes, while the pH value is 6.5 at the moment. Next, the insoluble materials are removed with centrifugal separation, and the soybean extract liquid is freeze-dried into powder. Thus, a composition of 9.4 g containing soluble isoflavones in an amount of 1.34 wt % is obtained. In the example, the recovery ratio of isoflavones from the whole soybeans is 63.0%.

Example 2

100 g of soybean hypocotyls from the America, in which the amount of isoflavones is 1.6 wt %, is dry-heated under a hot blast of 140° C. for 20 minutes using a gas roaster. After the treatment, the soybean hypocotyls is added with 500 ml of water in a pre-treatment, wherein the soybean hypocotyls contact with water under 20° C. for 2 hours. The liquid part is then removed with filtration. Next, the residue is added with 500 ml of water to implement an extraction process under 98° C. for 20 minutes, and then an extract liquid is obtained with filtration. The residue is further added with 100 ml of water to implement another extraction process under 98° C. for 20 minutes, and then another extract liquid is obtained with the same operation. The two extract liquids are mixed into a soybean extract liquid. In the soybean extract liquid, the amount of isoflavones in total solid content is 6.0 wt %, the crude protein content is 22 wt %, and the lipid content is 0.5 wt %. The soybean extract liquid is cooled to 10° C. and kept at the same temperature for 30 minutes, while the pH value is 6.5 at the moment. Next, the insoluble materials are removed with centrifugal separation, and the soybean extract liquid is freeze-dried into powder. Thus, a composition of 18.7 g containing soluble isoflavones in an amount of 6.06 wt % is obtained. In the example, the recovery ratio of isoflavones from the soybean hypocotyls is 70.8%.

Example 3

10 g of whole soybeans from the America, in which the amount of isoflavones is 0.2 wt %, is added with 500 ml of water in a pre-treatment, wherein the soybeans contact with water under 20° C. for 2 hours. The liquid part is then removed with filtration. Next, the residue is added with 500 ml of water to implement extraction process under 98° C. for 20 minutes, and then an extract liquid is obtained with filtration. The residue is further added with 500 ml of water to implement another extraction process under 98° C. for 20 minutes, and then another extract liquid is obtained with the same operation. The two extract liquids are mixed into a soybean extract liquid. In the soybean extract liquid, the amount of isoflavone in total solid content is 1.3 wt %, the crude protein content is 24 wt %, the lipid content is 1.0 wt %, and the pH value is 6.5 at the moment. Next, a neutral protease from *Bacillus subtilis* (Orientase 90N, produced by Hankyu Kyoei Bussan Inc.) is added in an amount of 0.9 wt % relative to the total solid content, and the reaction is carried out under 50° C. for 1 hour. Next, the soybean extract liquid is heated under 80° C. for 30 minutes to deactivate the enzyme, and the pH value is adjusted to 3.5 by adding $HCl_{(aq)}$. The soybean extract liquid is cooled to 10° C. and placed still for 30 minutes. Next, the insoluble materials are removed with centrifugal separation, and the soybean extract liquid is neutralized by adding NaOH to have a pH value of 6.5. The soybean extract liquid is then freeze-dried into powder, and a composition of 8.8 g containing soluble isoflavones in an amount of 1.40 wt % is obtained. In the example, the recovery ratio of isoflavones from the whole soybeans is 61.6%.

Example 4

100 g of soybean hypocotyls as obtained in Example 2, in which the amount of isoflavones is 1.6 wt %, is added with 500 ml of water in a pre-treatment, wherein the soybeans contact with water under 20° C. for 2 hours. The liquid part is then removed with filtration. Next, the residue is added with 500 ml of water to implement an extraction process under 98° C. for 20 minutes, and then an extract liquid is obtained with filtration. The residue is further added with 500 ml of water to implement another extraction process under 98° C. for 20 minutes, and then another extract liquid is obtained with the same operation. The two extract liquids are mixed into a soybean extract liquid. In the soybean extract liquid, the amount of isoflavone in total solid content is 6.0 wt %, the crude protein content is 22 wt %, the lipid content is 0.5 wt %, and the pH value is 6.5 at the moment. Next, a neutral protease from *Bacillus subtilis* (Orientase 90N, produced by Hankyu Kyoei Bussan Inc.) is added in an amount of 0.9 wt % relative to the total solid content, and the reaction is carried out under 50° C. for 1 hour. Next, the soybean extract liquid is heated under 80° C. for 30 minutes to deactivate the enzyme, and the pH value is adjusted to 3.5 by adding $HCl_{(aq)}$. The soybean extract liquid is cooled to 10° C. and placed still for 30 minutes. Next, the insoluble materials are removed with centrifugal separation, and the soybean extract liquid is neutralized by adding NaOH to have a pH value of 6.5. The soybean extract liquid is then freeze-dried into powder, and a composition of 15.5 g containing soluble isoflavones in an amount of 6.32 wt % is obtained. In the example, the recovery ratio of isoflavones from the soybean hypocotyls is 61.2%.

Example 5

A soybean extract liquid as obtained in Example 4 is added with $HCl_{(aq)}$ to have a pH value of 3.5 without the protease treatment, and is cooled to 10° C. and placed still for 30 minutes. After the insoluble materials are removed with centrifugal separation, the soybean extract liquid is neutralized by adding NaOH to have a pH value of 6.5. The soybean extract liquid is then freeze-dried into powder, and a composition of 10.3 g containing soluble isoflavones in an amount of 4.72 wt % is obtained. In the example, the recovery ratio of isoflavones from the soybean hypocotyls is 30.4%. Though the solubility of the composition in water is relatively high, the recovery ratio of isoflavones gets low since a part of the isoflavones are removed together with the insoluble materials during the removal step under acidic condition.

Example 6

10 g of the composition containing soluble isoflavones as obtained in Example 4 is dissolved in 100 ml of water, and then the solution is conducted through a column (ø 2.5 cm×20 cm) packed with 100 ml of an activated synthetic adsorbent of styrenedivinylbenzene type (Diaion HP-20, produced by Mitsubishi Chemical Corporation) in a flow rate of 100 ml/hr. Next, the adsorbent is washed with 200 ml of water and 200 ml of 20% ethanol in sequence to remove impurities, and then the target materials are eluted with 300 ml of 70% ethanol. After being condensed under low pressure to remove ethanol, the solution is freeze-dried into a composition of 1.5 g containing soluble isoflavones in an amount of 26.2 wt %.

Utility in the Industry

By using the method of this invention, a composition containing isoflavones can be obtained with a high solubility 100 or more times the solubility of pure isoflavone and good stability preventing precipitation and cloudiness after long-term preservation under refrigeration. The isoflavones can be easily obtained in their natural states with a high recovery ratio using soybean materials as raw materials without addition of solubilizing agents or chemical modification. Therefore, the scope of the applications of isoflavones in food-related fields can be significantly expanded, and this invention should have great significance to the industry.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A method for producing a soluble composition containing isoflavones, comprising:

performing a water extraction to obtain a soybean extract liquid from soybean hypocotyls;

treating the soybean extract liquid with a protease preparation having a low β-glucosidase activity so as to reduce the formation of aglycone which is formed by breaking a β-glucoside bond between an aglycone moiety and a saccharide moiety of isoflavone glucoside;

adjusting the pH value of the soybean extract liquid so that the pH is $\geq 2$ and <5.5 and adjusting the temperature to 0-17° C. after the soybean extract liquid is treated with the protease preparation and removing insoluble materials that are generated after the pH value and the temperature of the soybean extract liquid are adjusted from the soybean extract liquid.

2. The method of claim 1, wherein the amount of isoflavones is 0.2-20 wt %, the crude protein content is 30 wt % or less, and the lipid content is 4 wt % or less in the total solid content of the soybean extract liquid after removing insoluble materials.

3. The method of claim 1, wherein the soybean extract liquid is obtained from soybean hypocotyls using a physical treatment not destroying soybean cells or without a physical treatment.

* * * * *